United States Patent [19]

Lepie

[11] Patent Number: 5,074,100

[45] Date of Patent: Dec. 24, 1991

[54] RAIL STRUCTURE APPARATUS AND METHOD OF FABRICATING MATCHBOOK-LIKE ARTICLES CONTAINING WOUND DENTAL FLOSS AND THE LIKE

[76] Inventor: Eric J. Lepie, 2717 N. Magnolia, Tucson, Ariz. 85712

[21] Appl. No.: 652,932

[22] Filed: Feb. 8, 1991

[51] Int. Cl.$^5$ .................................. A61L 17/02
[52] U.S. Cl. .................................. 53/430; 53/116; 53/395; 206/63.5; 206/396
[58] Field of Search ............... 53/430, 116, 395, 394; 206/63.5, 396, 395, 388, 397, 473, 472, 105, 104, 227, 368, 369

[56] References Cited

U.S. PATENT DOCUMENTS

| | | | |
|---|---|---|---|
| 1,671,947 | 5/1928 | Hutchinson | 53/395 |
| 1,829,994 | 11/1931 | Langley | 53/395 |
| 2,109,318 | 2/1938 | Lichter | 206/64 |
| 2,336,234 | 12/1942 | Evans | 206/29 |
| 2,364,085 | 12/1944 | Martinek | 53/395 X |
| 3,438,486 | 4/1969 | Pinkas | 205/56 |
| 3,532,477 | 10/1970 | De Capitani | 53/395 X |
| 4,574,957 | 3/1986 | Stead | 206/388 X |
| 4,579,221 | 4/1986 | Corella | 206/388 X |
| 5,024,324 | 6/1991 | Whittaker | 53/430 X |

*Primary Examiner*—James F. Coan
*Attorney, Agent, or Firm*—Victor Flores

[57] ABSTRACT

A rail structure usable in the manufacture of packaged goods in matchbook-like form, especially threadlike goods such as dental floss. The rail structure conforms to attachment tooling and matchbook cover design constraints relating to similar rail structure used in the manufacture of matchbooks. The rail structure can accommodates either horizontal or vertical winding processes, according to the particular rail structure used for securing the threadlike article. The structure used for horizontal winding is an elongated rail structure formed having alternating article support portions separated by alternating notches. The matchbook-like array is formed by two side by side arrangement of the horizontally wound rail structure. The rail structure used for vertical winding is an elongated rail having upper and lower notches for securing the threadlike article. The lower notches have a deep V-shape portion for ease of detachment of the threadlike articles.

20 Claims, 3 Drawing Sheets

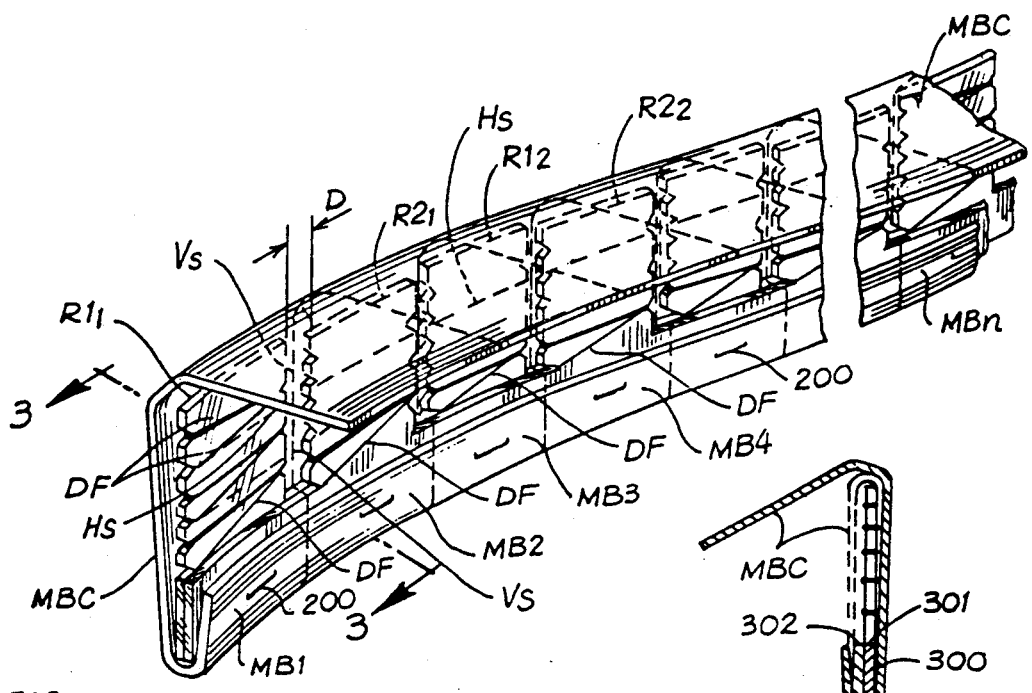
Fig. 2
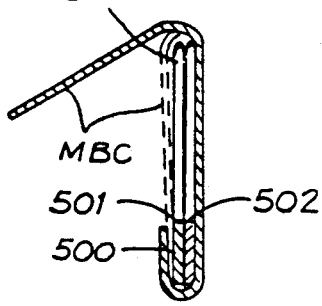
Fig. 3A
Fig. 3B
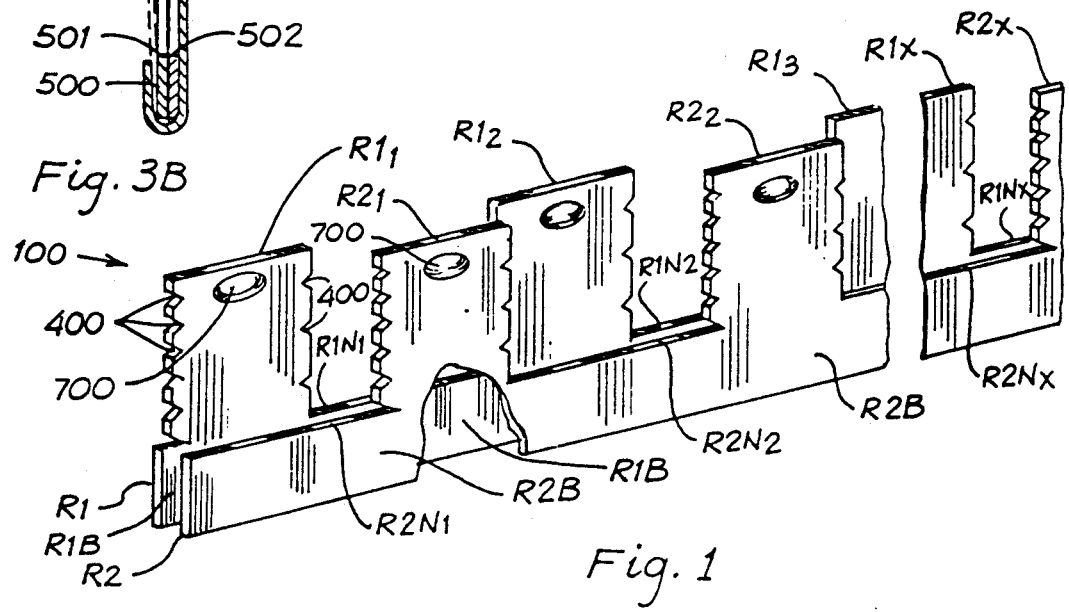
Fig. 1

RAIL STRUCTURE APPARATUS AND METHOD OF FABRICATING MATCHBOOK-LIKE ARTICLES CONTAINING WOUND DENTAL FLOSS AND THE LIKE

FIELD OF THE INVENTION

This invention relates to rail structure used in manufacturing matchbook and matchbook-like articles. More particularly, the present invention relates to rail structure used in manufacturing matchbook-like articles whose content is wound onto the rail structure and which rail structure must conform to machinery constraints favoring manufacture of actual matchbooks.

DESCRIPTION OF THE PRIOR ART

The closest prior art relating to the present invention includes rail structure apparatus used in the matchbook manufacturing industry. In that industry, matchbooks are formed in an array comprising a pair of elongated match-containing strips, or matchbook rail structures arranged in a side by side manner. An elongated outer folded cover is attached during the manufacturing process using stapling tooling that sandwiches the side by side arrangement of the elongated match containing matchbook rail structures. The task of providing, or dispensing articles of manufacture, other than matches, in matchbook-like form has been previously addressed by others, see for example, U.S. Pat. No. 2,109,318 teaching a mending kit packaged in a matchbook-like structure. U.S. Pat. Nos. 2,336,234 and 3,438,486 teaching the use of a matchbook structure to support various personal care and other personal utility devices. The rail structure used to form these matchbook structure do not, however, address the constraints presented to applicant, namely: (1) that the rail structure that is sandwiched between the foldable matchbook cover must be equivalent to the rail structure used in the manufacture of matchbooks, if the same stamping, or attachment tooling is to be used, and (2) that the structure must accommodate a winding process for threadlike articles, such as small lengths of dental floss.

Thus, while the prior art has taught the use of the matchbook structure for detachably supporting a variety of personal care accessories, the prior art has failed to provide compatible article support rail structure that capitalizes on using the same tooling having design constraints centered around the rail structure used in matchbook manufacturing. Further, the prior art has failed to provide a rail structure having the above requisite characteristics that also accommodates an article of manufacture to be wound thereon a portion of the rail structure.

Therefore, a need is seen to exist for a rail structure usable in the manufacture of packaged goods in matchbook-like form, especially threadlike goods such as dental floss, that conform to attachment tooling constraints relating to a rail structure used in the manufacture of matchbooks.

More particularly, a need is seen to exist for a rail structure that meets the prior art tooling constraints and that also accommodates a winding process for securing threadlike articles of manufacture to the article support portion of the rail structure.

Even more particularly, a need is seen to exist for a rail structure apparatus that not only meets the prior art tooling constraints and the winding process requirements, but that also economizes on the structure material used by being formed in sets according to a predetermined pattern consistent with the tooling constraints and wounding process requirements.

SUMMARY OF THE INVENTION

Accordingly, the primary object of the present invention is to provide a rail structure usable in the manufacture of packaged goods in matchbook-like form, especially threadlike goods such as dental floss, that conform to attachment tooling constraints relating to a rail structure used in the manufacture of matchbooks.

A closely related object of the present invention is to provide a rail structure that meets the prior art tooling constraints and that also accommodates a winding process for securing threadlike articles of manufacture to the article support portion of the rail structure.

Another related object of the present invention is to provide a rail structure apparatus that not only meets the prior art tooling constraints and the winding process requirements, but that also economizes on the structure material used by being formed in sets according to a predetermined pattern consistent with the prior art tooling constraints and winding process requirements.

The foregoing objects are accomplished by providing a rail structure apparatus for use in packaging manufactured articles in matchbook-like form, comprising, in one embodiment, an elongated, flat and substantially thin rail structure having an elongated bearing portion, said bearing portion having a plurality of alternating notched portions and a plurality of alternating article support portions integrally and longitudinally adjacent thereto.

The alternating notched portions and the plurality of alternating article support portions being spaced apart to allow portions of threadlike articles of manufacture to be wound onto one of said plurality of article support portions without adjacent ones of said plurality of article support portions interfering with the winding process.

In a method of packaging articles of manufacture in matchbook-like form, the elongated rail structure can be combined with an identical elongated rail structure for forming an elongated array of detachable matchbook-like units containing suitably designed manufactured articles for being supported on respective ones of said article support portions. The said combination results in obtaining a target cross section in each matchbook-like unit comprising of a first bearing portion thickness associated with a notched portion of one rail structure and a second bearing portion thickness associated with an article support portion of the other rail structure, said target cross section being equivalent to a reference cross section of a side by side matchbook rail structure arrangement used in manufacturing matchbooks.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

BRIEF DESCRIPTION OF THE DRAWINGS

FIG. 1 is a perspective view of the present invention illustrating a pair of rail structures in a side by side arrangement of the respective bearing portions and the alternating notch and article support portions, the article support portions having the peripheral notches for winding individual portions of dental floss and an depression for securing a second article of manufacture such as a mint.

FIG. 2 is a perspective view of the present invention illustrating an elongated array of detachable matchbook-like units containing suitably designed manufactured articles, such as dental floss, that are supported on respective ones of the rail structure article support portions.

FIG. 3A is a cross sectional view taken along line 3—3 in FIG. 2 illustrating, primarily, a target cross section of a matchbook-like unit that includes a first bearing portion thickness associated with a notched portion of one rail structure and a second bearing portion thickness associated with an article support portion of the other rail structure.

FIG. 3B illustrates a reference cross sectional view of a matchbook structure having layered matchbook rail structure that provides a reference cross section for determining the bearing portion's thickness to obtain the target cross section referred to in FIG. 3A.

DESCRIPTION OF THE PREFERRED EMBODIMENT

Figure 4:
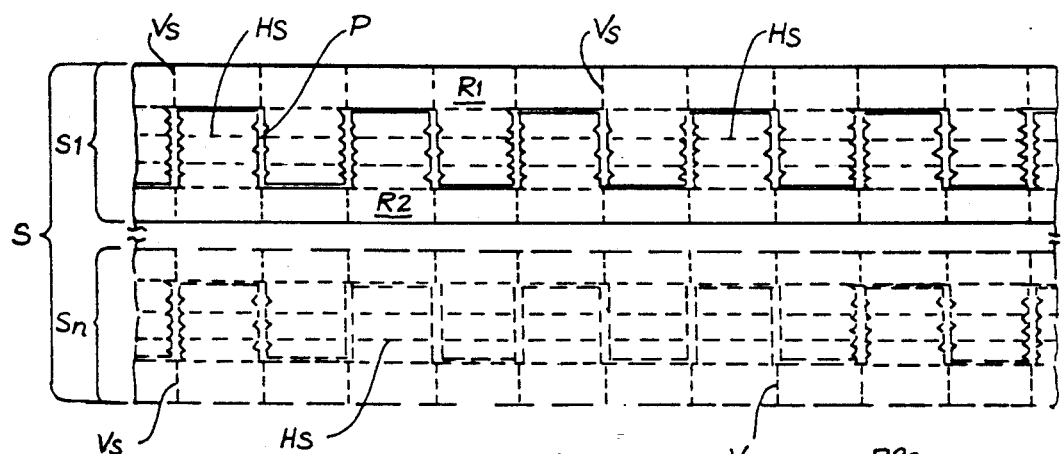
FIG. 4 is a layout view of a partial sheet of material, such as a cardboard material, illustrating the formation of sets of complementing rail structure members, each set being cut according to a pattern that produces in each rail structure member, alternating notch portions, alternating article support portions and vertical and horizontal scores.

According to the problem presented to the applicant, in order to provide dental floss in a matchbook-like packages utilizing existing tooling, the rail support for the dental floss must conform to the existing rail supports used in the manufacture of matchbooks. Additionally, the dental floss must be secured to the rail support using conventional thread winding techniques. The present invention addresses the foregoing problems by providing, as shown in FIG. 1, a rail structure apparatus 100 in the form of a first and second rail structures R1 and R2. Each rail structure R1, R2 comprises an elongated, flat and substantially thin rail structure having an elongated bearing portion R1B, R2B, said bearing portion R1B, R2B having a plurality of alternating notched portions R1N(1−x), R2N(1−x) and a plurality of alternating article support portions R1(1−x), R2(1−x) integrally and longitudinally adjacent thereto useable for winding dental floss thereon.

The constraints for using the same tooling, as is used in the matchbook manufacturing process, includes being able to adapt a proposed rail member containing a product, other than matches, to the matchbook structure's elongated matchbook cover sheet for attachment using a particularly sized attachement means. FIG. 3B illustrates a reference cross section of a matchbook structure 503 having two side-by-side match rails attached at a folded end of cover MBC, and whose individual cross section thickness 501 and 502 combine to form a reference thickness 500. It should be appreciated, that while one rail structure, such as either R1 or R2, could be provided with the reference thickness 500 to meet the constraints, alternating notches of R1, R2 produce too much waste of the matchbook cover sheet, i.e. at every notch. Thus, as best seen by referring to FIGS. 2 and 3A, rails R1 and R2 are arranged in a side by side relationship for forming an elongated array of detachable matchbook-like units MB(1−n) using the same matchbook cover MBC and staple means 200 as would be used to produce matchbook 503. The side by side arrangement of R1 and R1 results in a first alignment of respective ones of said bearing portions R1B, R2B that overlay each other and a second alignment of respective ones of said notched portions, R1N1, R1N2, ... R1Nx, (R2N1, R2N2, ... R2Nx) overlaying respective ones of said article support portions, R21, R22 ... R2x, (R11, R12,...R1x). The first alignment results in a target cross section 300 made up of the respective thickness 301, 302 of R1B and R2B to satisfy the constraint of the reference thickness. The structural side by side arrangement of R1 and R2 not only enables use of the same tooling as is used in the manufacture of matches for packaging other product in matchbook form, it also optimizes the use of the entire matchbook sheets for the new product.

Referring back to FIG. 1, embodiment 100 contemplates a horizontal winding process objective for securing threadlike manufactured articles, such as dental floss DF depicted in FIG. 2, to the article supports portions R1(1−x), R2(1−x). To accomplish this objective, alternating large notches R1N(1−x), R2N(1−x) are formed to provide sufficient space d (see FIG. 5A) to encircle the article support portion during the winding process. The right and left laterally opposed arrangement of notches 400 on the article support portions fixedly secure the individual threadlike article to the article support portion.

Further, as seen from FIG. 4, the alternating large notch arrangement R1N(1−x), R2N(1−x) provides an opportunity to provide a pattern P for cutting complementing sets S(1−n) of rails R1, R2 from a larger sheet of material S, typically a 15 inch long, variable depth, cardboard sheet. Pattern P includes a plurality of vertical scores Vs and horizontal scores Hs that enable detachment of individual match-book like structures from the matchbook-like array and the detachment of the individual portions of dental floss DF from a particular article attachment portion in any individual matchbook-like structure. The pattern also provides adequate spacing D for detachment of the individual matchbook-like structure, see FIG. 2.

Figure 5B:
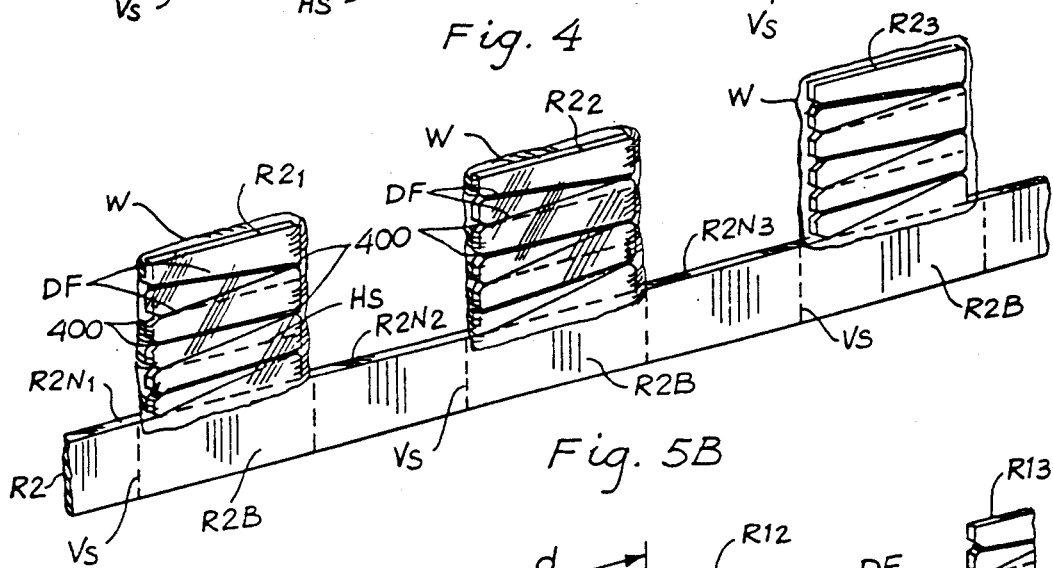
FIGS. 5A and 5B are perspective views of a first and second rail structure members illustrating the securement of a plurality of dental floss portions to the article support portions about peripheral notches and further illustrating in FIG. 5A a representative translucent wrapping for sealing the secured dental floss portion.
Figure 5A:
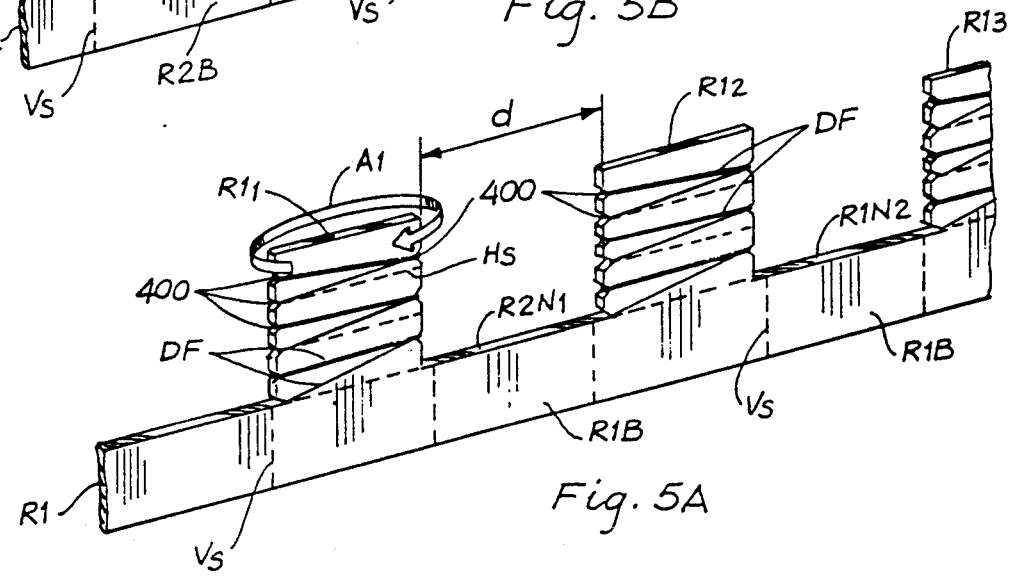

FIGS. 5A and 5B illustrate prepared stages of rail structure members R1 and R2. FIG. 5A illustrates the horizontal winding securement, as indicated by arrow A1, of a plurality of dental floss portions DF to the article support portions R1(1−x) and R2(1−x) about right and left laterally opposed notches 400, the notches R1N(1−x), R2N(1−x) having a space d, sufficient to perform the winding operation. FIG. 5B further illustrates a rail structure product wrapping operation, showing a representative translucent wrapping W used for sealing the secured dental floss portion. As indicated in FIG. 1, a second article of manufacture, such as breath mint, can be packaged in a depression 700 which, if provided, can also be sealed with the dental floss DF.

Figure 6:
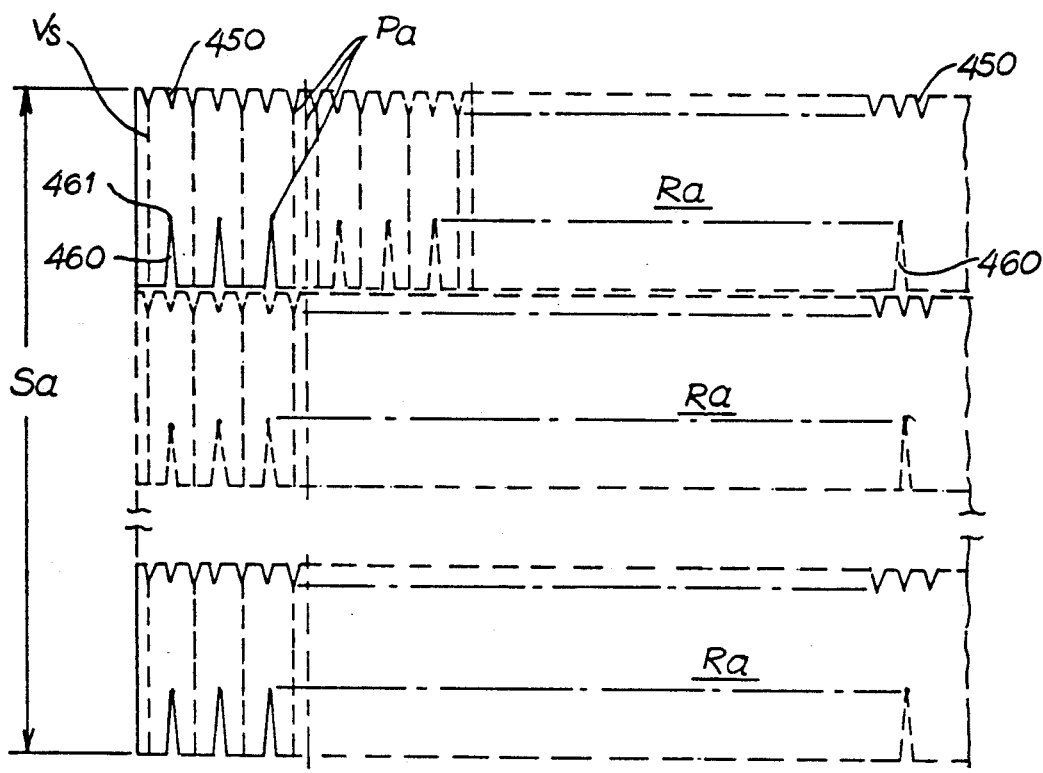
FIG. 6 is a layout view of a partial sheet of material, such as a cardboard material, illustrating the formation of a plurality of rail structure members for an alternative design adapted for a vertical winding process that secures threadlike articles, such as dental floss, to the rail and adapted to enable unimpeded subsequent detachment of the secured article.

As stated previously, embodiment 100 contemplates a horizontal winding process for securing threadlike manufactured articles to the article supports portions R1(1−x), R2(1−x), as depicted in FIG. 5A. As depicted in FIG. 6, alternative rail embodiment Ra is provided for enabling a vertical winding process for securing the threadlike manufactured articles, while still conforming to the constraints of using the same tooling that secures matchbook rails to a matchbook cover. As best seen in FIG. 6, a plurality of rails Ra may be formed from a sheet of cardboard material Sa. Each rail Ra is cut according to a pattern Pa that forms upper and lower laterally opposed notches 450 and 460. Notches 460 have a distinctive deep V-shape termination 461 that have utility in detachment of the threadlike articles. The detachment of small portions of Ra is accomplished by including a plurality of vertical scoring Vs.

Figures 7, 8, 9, 10:
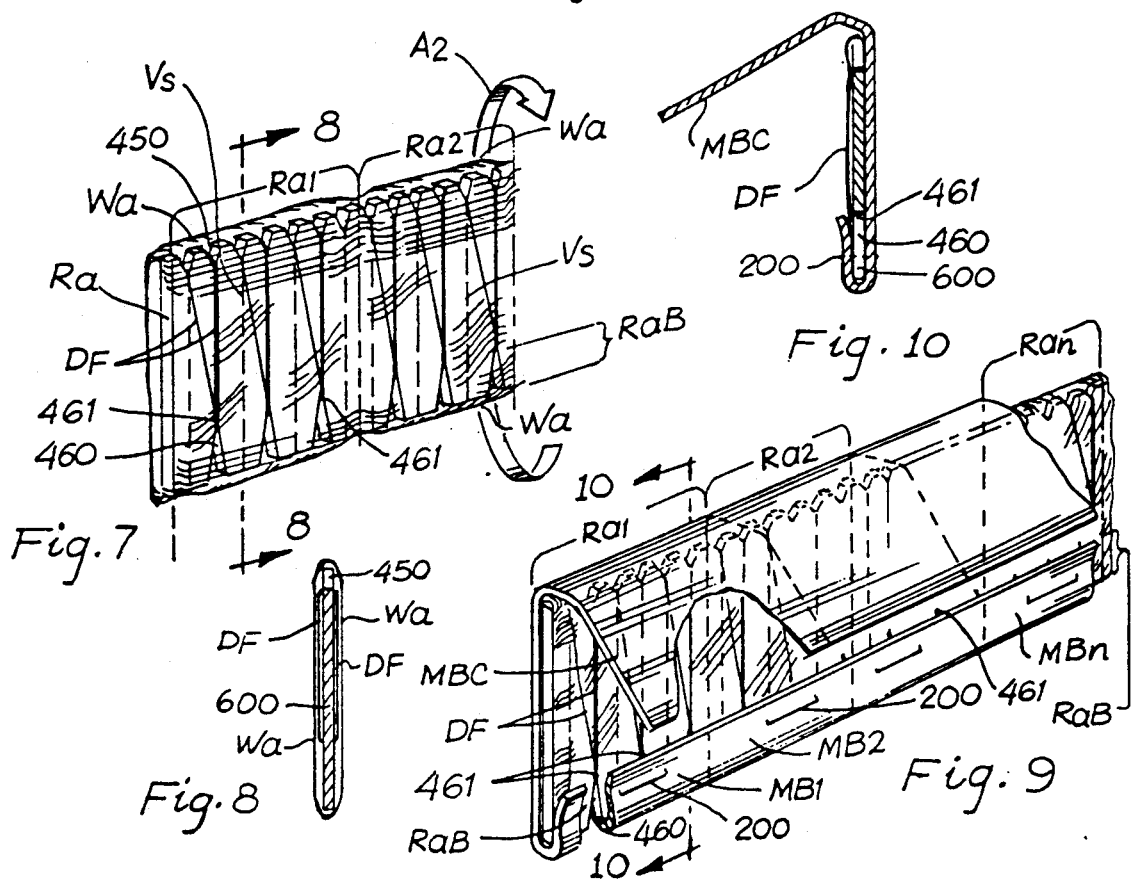
FIG. 7 is a perspective view of the alternative rail structure design illustrating the securement of a plurality of dental floss portions to the article support portions about upper and lower, laterally opposed notches and covered with translucent wrapping for sealing the secured dental floss portion.
FIG. 8 is a cross sectional view taken along line 8—8 in FIG. 7 illustrating the sealed dental floss packaged on a rail section ready for combining with a matchbook-like cover.
FIG. 9 is a perspective view of the present invention illustrating an elongated array of detachable matchbook-like units using the alternative rail structure illustrated in FIG. 6.
FIG. 10 is a cross sectional view taken along line 10—10 in FIG. 9 illustrating, primarily, an alternative target cross section of the matchbook-like unit that includes a single bearing portion thickness associated with the lower notched portion of the alternative rail structure illustrated in FIG. 6.

Referring now to FIG. 7, each rail Ra can be manipulated by winding machinery to wind portion of threadlike article onto corresponding opposed notches 450 and 460, such as dental floss DF and as generally indicated by arrow A2. The marginal area encompassing 460 has bearing portion RaB that defines the attachment region for attaching the folded end of matchbook MBC. It should be noted that RaB, does not include termination 461 that holds the loop ends of the wound dental floss DF. Having termination 461 outside the region RaB results in easy, unimpeded detachment at Vs of the individual dental floss portions from the article support members Ra(1−n). Each rail Ra with the secured dental floss onto notches 450 and 460 may be wrapped as desired as indicated by wrapping Wa.

Since part of the constraints presented to the inventor were that equivalent rail structure cross section must be provided to utilize the same tooling as used in matchbook manufacturing, rail structure Ra is provided with a cross section 600 that is equivalent to the matchbook rail structures 500, see FIGS. 8, 10 and 3B.

FIG. 9 shows a matchbook-like array containing packaged dental floss on a rail Ra secured to the matchbook-like cover MBC at RaB using staples 200. The array can be sectioned at units MB(1−n) containing article support portions Ra(1−n) with dental floss DF.

Therefore, while the present invention has been shown and described herein in what is believed to be the most practical and preferred embodiments, it is recognized that departures can be made therefore within the scope of the invention, which is therefore not to be limited to the details disclosed therein but is to be accorded the full scope of the claims so as to embrace any and all equivalent apparatus.

I claim:

1. A method of manufacturing articles in matchbook-like form, said method comprising the steps of:
   (a) providing a first and second elongated rail structure, each of said first and second rail structure having an elongated bearing portion, said bearing portion having a plurality of alternating notched portions and a plurality of alternating article support portions integrally and longitudinally adjacent thereto;
   (b) providing a plurality of manufactured articles, each one of said plurality of articles being suitably designed for detachable securement to one of said article support portions;
   (c) providing an elongated, foldable sheet structure and attachment means for use in forming an outer cover of a matchbook-like array structure;
   (d) securing respective ones of said plurality of articles to each of said article support portions on said first and second elongated rail structures;
   (e) arranging said first and second elongated rail structures for forming said matchbook-like array structure by aligning respective bearing portions to overlay each other and aligning respective ones of said notched portions to overlay respective ones of said article support portions;
   (f) forming said matchbook-like array structure by attaching said foldable sheet structure to said arranged first and second rail structures using said attachment means at spaced points on said bearing portions corresponding to all locations of said plurality of alternating article support portions; and
   (g) detaching individual matchbook-like units from said array utilizing suitably spaced scores located on said provided first and second rail structures and said sheet structure.

2. A method of manufacturing articles in matchbook-like form as recited in claim 1, wherein:
   said step of providing a plurality of manufactured articles includes providing dental floss; and
   said step of securing respective ones of said plurality of articles, further includes the step of sealing said dental floss with a suitable wrapping medium to prevent contamination.

3. A rail structure apparatus for use in packaging manufactured articles in matchbook-like form, said rail structure apparatus comprising:
   an elongated, flat and substantially thin rail structure having an elongated bearing portion, said bearing portion having a plurality of alternating notched portions and a plurality of alternating article support portions integrally and longitudinally adjacent thereto,
   said elongated rail structure being combinable with an identical elongated rail structure for forming an elongated array of detachable matchbook-like units containing suitably designed manufactured articles for being supported on respective ones of said article support portions.

4. A rail structure apparatus as recited in claim 3 wherein:

said alternating notched portions and said plurality of alternating article support portions being spaced apart to allow portions of threadlike articles of manufacture to be wound onto one of said plurality of article support portions without adjacent ones of said plurality of article support portions interfering with the winding process.

5. A rail structure apparatus as recited in claim 4 wherein:

said elongated, flat and substantially thin rail structure and said identical elongated rail structure being arranged in a side by side relationship for forming said elongated array of detachable matchbook-like units, said relationship including a first alignment of respective ones of said bearing portions that overlay each other and a second alignment of respective ones of said notched portions overlaying respective ones of said article support portions.

6. A rail structure apparatus as recited in claim 5 wherein:

said relationship results in obtaining a target cross section in each matchbook-like unit comprising of a first bearing portion thickness associated with a notched portion of one rail structure and a second bearing portion thickness associated with an article support portion of the other rail structure, said target cross section being equivalent to a reference cross section of a side by side matchbook rail structure arrangement used in manufacturing matchbooks;

said threadlike article of manufacture comprises dental floss; and said article support portions having a depression for securing a second article of manufacture.

7. A rail structure apparatus as recited in claim 3, wherein:

said elongated, flat and substantially thin rail structure and said identical elongated rail structure being arranged in a side by side relationship for forming said elongated array of detachable matchbook-like units, said relationship including a first alignment of respective ones of said bearing portions that overlay each other and a second alignment of respective ones of said notched portions overlaying respective ones of said article support portions.

8. A rail structure apparatus as recited in claim 7, wherein:

said relationship results in obtaining a target cross section in each matchbook-like unit comprising of a first bearing portion thickness associated with a notched portion of one rail structure and a second bearing portion thickness associated with an article support portion of the other rail structure, said target cross section being equivalent to a reference cross section of a side by side matchbook rail structure arrangement used in manufacturing matchbooks.

9. A rail structure apparatus as recited in claim 3, wherein:

each one of said plurality of article support portions comprises a geometric protrusion protruding from an adjacent portion of said bearing portion, each said protrusion having peripheral notches for securing threadlike articles of manufacture thereto.

10. A rail structure apparatus as recited in claim 9, wherein:

said alternating notched portions and said plurality of alternating article support portions being spaced apart to allow portions of said threadlike articles of manufacture to be wound onto said geometric protrusion without adjacent geometric protrusions interfering with the winding process; and said elongated rail structure having a plurality of alternating vertical scores for delineating individual rail structure members associated with said detachable matchbook-like units.

11. A rail structure apparatus as recited in claim 9, wherein:

said threadlike articles of manufacture comprises dental floss; and said geometric protrusion further comprises a depression for securing a second article of manufacture and horizontal scores for delineating detachable individual dental floss portions.

12. A rail structure apparatus as recited in claim 3 wherein:

said rail structure comprises a rail structure member of a set of complementing rail structure members formed from a sheet of suitable material, said rail structure member being formed from an elongated section of said sheet of material, said elongated section being cut according to a pattern that produces said set of complementing rail structure members, each rail structure member having said elongated bearing portion, said plurality of alternating notched portions and said plurality of alternating article support portions.

13. A rail structure apparatus for use in packaging manufactured articles in matchbook-like form, said rail structure apparatus comprising:

a first and second elongated, flat and substantially thin rail structures, each rail structure having an elongated bearing portion, said bearing portion having a plurality of alternating notched portions and a plurality of alternating article support portions integrally and longitudinally adjacent thereto, said first and second rail structures being arranged in a side by side relationship for forming an elongated array of detachable matchbook-like units containing suitably designed manufactured articles supported on respective ones of said article support portions.

14. A rail structure apparatus as recited in claim 13, wherein:

said relationship includes a first alignment of respective ones of said bearing portions that overlay each other and a second alignment of respective ones of said notched portions that overlay respective ones of said article support portions, said relationship results in obtaining a target cross section in each matchbook-like unit comprising of a first bearing portion thickness associated with a notched portion of one rail structure and a second bearing portion thickness associated with an article support portion of the other rail structure, said target cross section being equivalent to a reference cross section of a side by side matchbook rail structure arrangement used in manufacturing matchbooks; and each one of said plurality of article support portions comprises a geometric protrusion protruding from an adjacent portion of said bearing portion, each said protrusion having peripheral notches for securing threadlike articles of manufacture thereto.

15. A rail structure apparatus as recited in claim 14, wherein:
   said alternating notched portions and said plurality of alternating article support portions being spaced apart to allow portions of said threadlike articles of manufacture to be wound onto said geometric protrusion without adjacent geometric protrusions interfering with the winding process; and
   said first and second elongated rail structures having a plurality of alternating vertical scores for delineating individual rail structure members associated with said detachable matchbook-like units.

16. A rail structure apparatus as recited in claim 15, wherein:
   said threadlike articles of manufacture comprises dental floss; and
   said geometric protrusion further comprises a depression for securing a second article of manufacture and horizontal scores for delineating detachable individual dental floss portions.

17. A rail structure apparatus for use in packaging manufactured articles in matchbook-like form, said rail structure apparatus comprising:
   a sheet of material for being formed into at least one set of complementing rail structure members,
   said at least one set of complementing rail structure members comprising a first elongated structure and a second elongated structure formed from an elongated section of said sheet of material, said elongated section being cut according to a pattern that produces an elongated bearing portion and a plurality of alternating notched portions and a plurality of alternating article support portions integrally and longitudinally adjacent to said bearing portion in each of said first and second elongated structures, said first and second elongated structures being combinable to form an elongated array of detachable matchbook-like units containing suitably designed manufactured articles for being supported on respective ones of said article support portions.

18. A rail structure apparatus for use in packaging threadlike manufactured articles in matchbook-like form using a foldable matchbook-like cover, said rail structure apparatus comprising:
   at least one elongated rail structure member, said at least one rail structure member comprising an elongated bearing portion for attachment to said foldable matchbook-like cover and a plurality of article support portions integrally and longitudinally adjacent to said bearing portion, said plurality of article support portions having a plurality of notches for wound securement of threadlike manufactured articles.

19. A rail structure apparatus for use in packaging threadlike manufactured articles as recited in claim 18, wherein:
   said plurality of notches comprise upper and lower laterally opposed, spaced notch members for allowing vertically wound securement of said threadlike manufactured articles, said lower spaced notch members being interspaced along said elongated bearing portion, said lower spaced notch members having a substantially deep V-shape portion that allows said vertically wound securement and unimpeded subsequent detachment of individual portions of said wound threadlike manufactured articles from said article support portion.

20. A rail structure apparatus for use in packaging threadlike manufactured articles as recited in claim 18, further comprising:
   a plurality of alternating notched portions separated by said plurality of article support portions, said plurality of alternating notched portions and said plurality of article support portions being integrally and longitudinally adjacent said elongated bearing portion; and
   said plurality of notches comprise right and left, laterally opposed, spaced notch members, that allows horizontally wound securement of individual portions of said threadlike manufactured articles.

* * * * *